United States Patent [19]

Hinds et al.

[11] 4,002,966
[45] Jan. 11, 1977

[54] APPARATUS FOR DETECTING IMPERFECTIONS ON THE WALL OF CYLINDRICAL CONTAINERS

[75] Inventors: James J. Hinds, LaGrange; Lawrence D. Stepenske, Darien, both of Ill.

[73] Assignee: National Can Corporation, Chicago, Ill.

[22] Filed: Feb. 21, 1975

[21] Appl. No.: 551,976

[52] U.S. Cl. ................................. 324/37
[51] Int. Cl.² .......................... G01R 33/12
[58] Field of Search ............ 324/34 R, 37, 40; 209/72, 81 R, 81 A, 111.8

[56] References Cited

UNITED STATES PATENTS

| | | | |
|---|---|---|---|
| 2,573,824 | 11/1951 | Baker | 209/81 A |
| 2,791,730 | 5/1957 | Stont | 324/41 |
| 2,860,777 | 11/1958 | Ortegren et al. | 209/81 R |
| 3,098,565 | 7/1963 | Fouse et al. | 324/34 R |
| 3,101,848 | 8/1963 | Uhlig | 209/72 |

FOREIGN PATENTS OR APPLICATIONS

| | | | |
|---|---|---|---|
| 159,327 | 12/1966 | U.S.S.R. | 324/37 |

*Primary Examiner*—Robert J. Corcoran
*Attorney, Agent, or Firm*—James E. Anderson; Ralph R. Rath

[57] ABSTRACT

A method and apparatus for detecting cracks or flaws in flanges on the ends of metal container bodies is disclosed herein. The method contemplates generating a magnetic field by passing a primary alternating current having a substantially constant rms value through an inductor means and moving the flange through the magnetic field while monitoring the rms value of the total current passing through the coil and comparing the magnitude thereof with a reference value. A signal is produced when the differential between the values of the total current and the reference exceeds a certain level. The apparatus consists of holding means for receiving and holding a container and means for rotating the holding means about an axis to expose different portions of the flange to a fixed probe positioned adjacent the flange.

11 Claims, 6 Drawing Figures

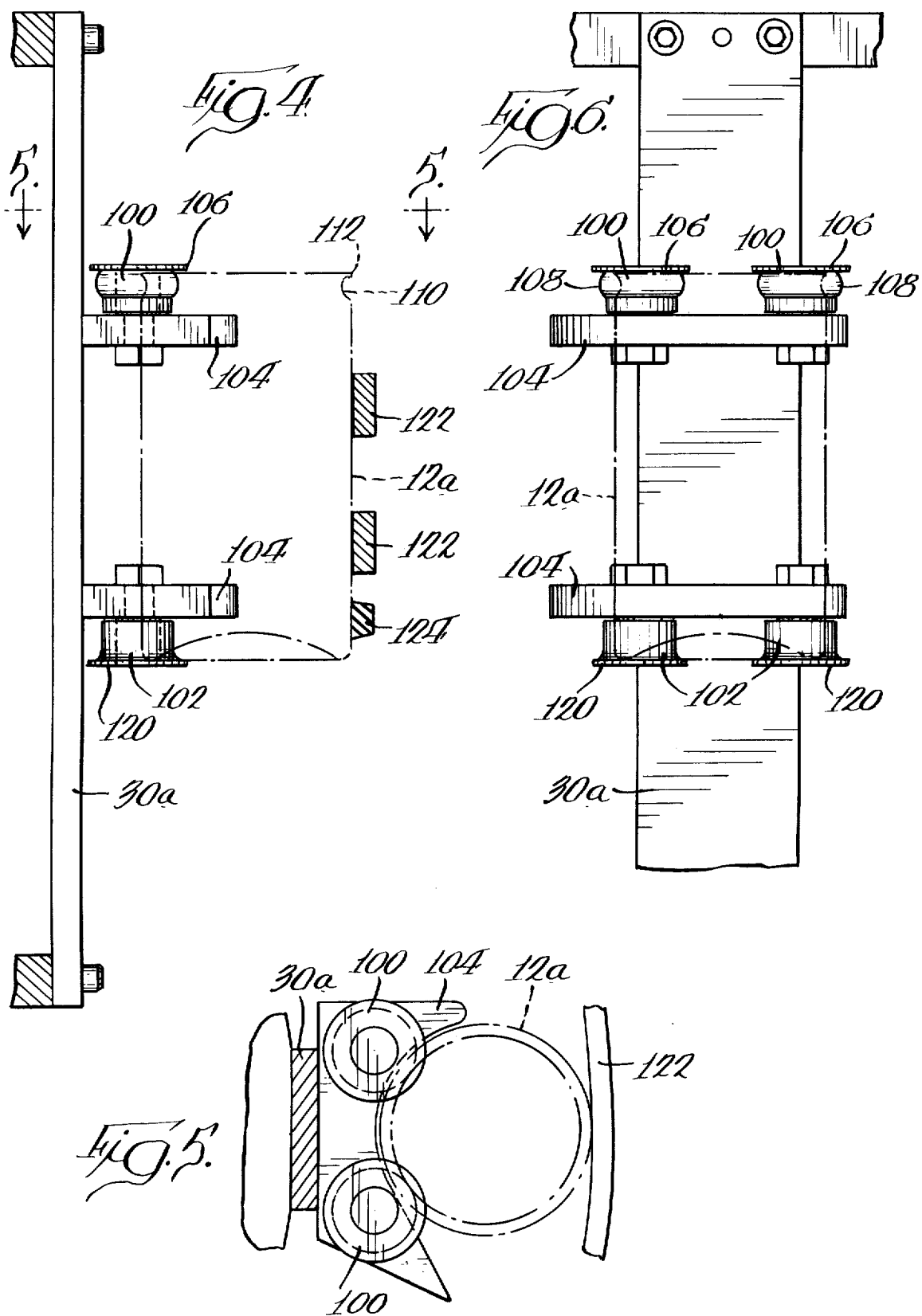

4,002,966

APPARATUS FOR DETECTING IMPERFECTIONS ON THE WALL OF CYLINDRICAL CONTAINERS

BACKGROUND OF THE INVENTION

The use of containers for packaging various beverages and other products has been common practice for many years. In recent years a new type of container has been developed which is commonly referred to as a "two-piece" container. In the formation of this type of container, a disc is drawn and ironed or extruded to form a cup which defines the bottom and side walls of a container. The free edge portion of the container body usually has a flange formed thereon which is utilized to attach an end panel to produce the finished product.

In the formation of this type of container, it is extremely important that the flange be devoid of any imperfections which may result in leakage after the container body and end panel have been seamed to each other.

Various types of proposals have been suggested for testing different portions of containers for flaws or imperfections. However, because of the speed at which the present day machinery is being operated, many of these devices are impractical for use on a production line.

While various methods of detection have been proposed, the speed and repetition rate in the formation of containers dictates that only non-contact test methods be used for detecting any flaws or imperfections.

One type of non-contact test that has been developed is known as the optical system wherein a light source is utilized as a portion of the test equipment. It has been found that such optical sytems must be quite sophisticated in order to produce an acceptable system which is not affected be ambient light, dirt or other variations.

Another type of test apparatus utilizes ultrasonics for detecting imperfections. However, this approach seems to be impractical due to the small dimensions of the cracks and the proximity of the cracks or imperfections to the edge of a flange.

The third type of non-contact system utilizes eddy currents as a sensing means. Various types of inspection apparatus have been proposed for inspecting various aspects of containers, and examples of such devices are shown in U.S. Pat. Nos. 3,700,101; 3,831,084; 3,609,527; and 3,495,166. While all of the above patents utilize the basic concept of eddy current detection of various types of flaws, none of these systems to date are capable of being utilized directly with a production line wherein containers must be checked in a short span of time.

Thus, there remains a need for a simple and inexpensive mechanism for detecting imperfections in containers and one which can be utilized as part of the production line in container manufacturing plants.

SUMMARY OF THE INVENTION

The present invention provides a testing apparatus which is capable of detecting flaws in a selected portion of a container body and the system is designed to be capable of being incorporated into an existing can manufacturing line without affecting the speed of operation. The system is automatically capable of removing containers having imperfections or flaws therein without interrupting the speed of the production line.

The method of the present invention contemplates generating a magnetic field having a predetermined value by passing an alternating current through an inductor means and then rotating a container body about its axis to pass all portions of a selected section of container body to be tested through the magnetic field while maintaining a fixed spacing between the tested portion of the container body and the inductor means and then comparing the rms value of the current producing the magnetic field with a reference value, and producing a signal when there is a predetermined difference between the two values.

Preferably, the testing is done while the containers are moved along a predetermined path and containers with imperfections are automatically removed from the container path by delaying the release of the containers from the test apparatus.

The test apparatus comprises fixed inductor means generating a magnetic field in response to an alternating current of a substantially constant rms value passing through the inductor means and holding means for holding the container body in the position where the selected section to be tested intersects the magnetic field. The apparatus also includes receiving means operatively connected to the inductor means for detecting variations in the current passing through the inductor means and comparing the rms values thereof wth a reference value. The apparatus also has switch means that cooperate with the holding means and the receiving means to indicate the presence of the container body in a test position in the holding means.

More specifically, the apparatus consists of a rotating hub that has a plurality of identical stations thereon, each of which include a holding means, a signal generating means, and receiving means so that container bodies may be inspected while they are moving along a continuous path. The receiving means produces a reject signal which takes the container bodies out of the predetermined path for reject when an imperfection is located.

The holding means, in one embodiment, consists of a pair of discs which are freely rotatable on a support and are movable towards and away from each other by a solenoid with a fixed belt engaging the holding means to rotate the container bodies as they are moving along the path.

In an alternate embodiment of the invention, the holding means consists of two pairs of contoured rollers that are adapted to engage the upper and lower ends of the container bodies with a driven belt engaging the container body on the opposite side for holding the container bodies against the contoured rollers and simultaneously rotating the containers.

BRIEF DESCRIPTION OF THE SEVERAL VIEWS OF THE DRAWINGS

FIG. 4 is a view similar to FIG. 3 showing a modified form of holding means;

FIG. 5 is a top plan view of the holding means as viewed along line 5—5 in FIG. 4; and FIG. 6 is an end view of the holding means shown in FIG. 4.

DETAILED DESCRIPTION

Figure 1:
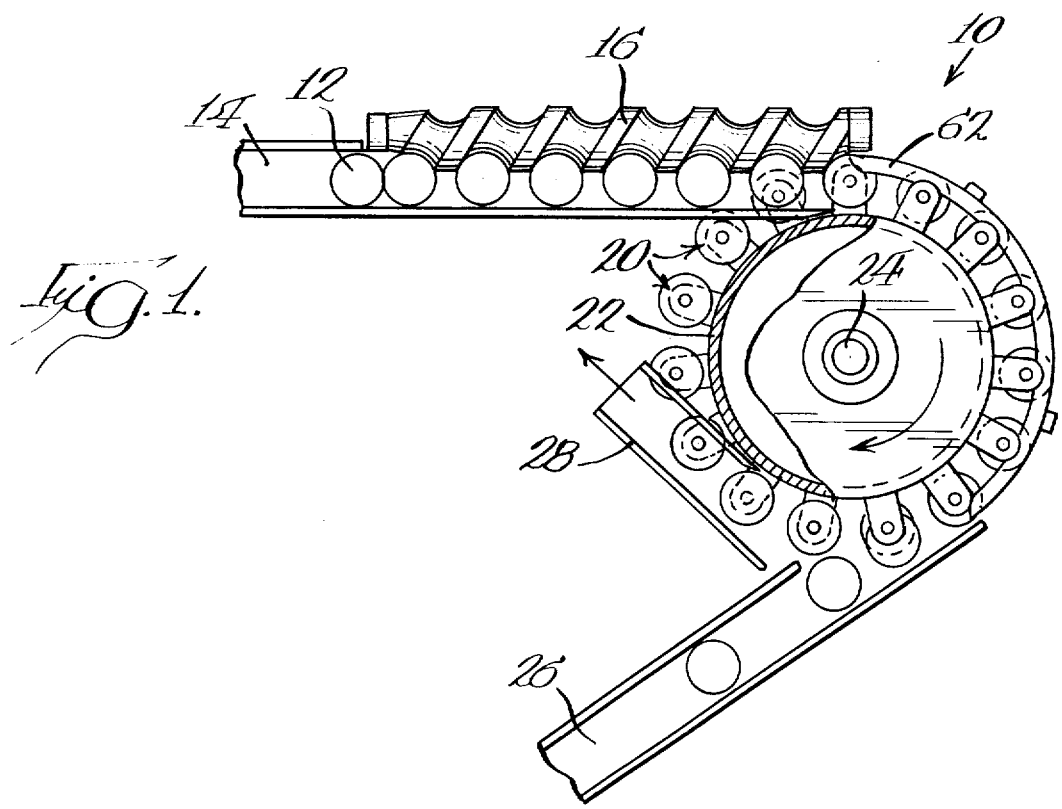
FIG. 1 is a fragmentary plan view, partially in section, showing an exemplary type of container inspection apparatus having the present invention incorporated therein.
Figure 2:
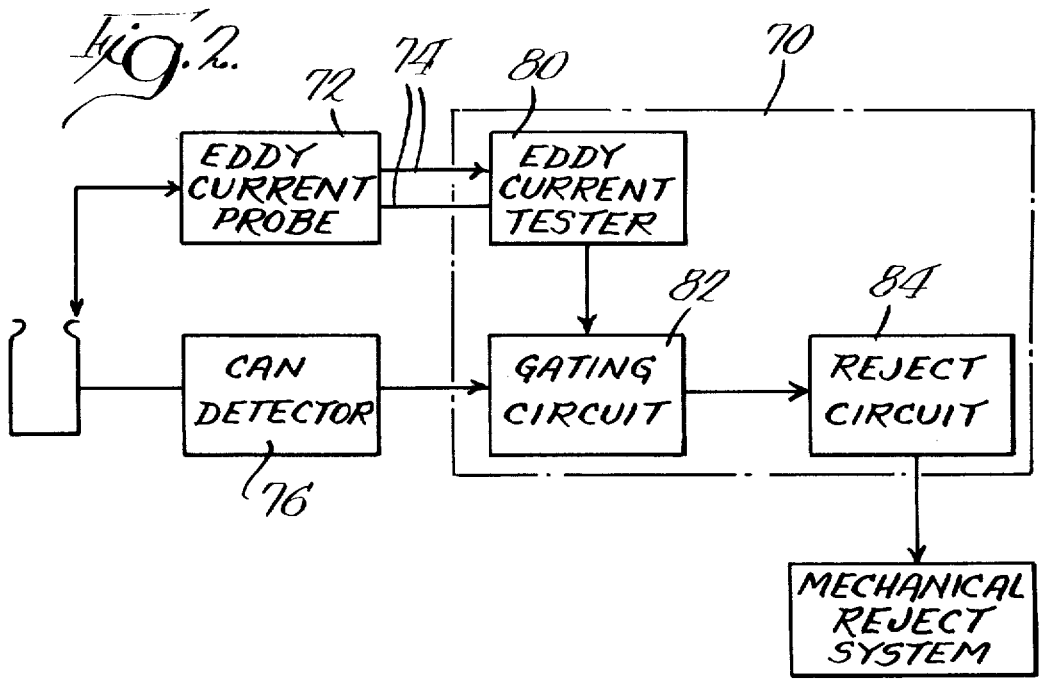
FIG. 2 is a block diagram of the electrical circuitry for the test apparatus.

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the invention to the embodiments illustrated.

In FIG. 1 of the drawings, there is shown a testing apparatus 10 constructed in accordance with the teachings of the present invention. Container bodies 12 are moved along a path defined by an inlet conveyor 14 by a continuously rotating feed screw 16 to produce a predetermined spacing between adjacent containers. The spaced containers continue their movement along the path and are received into testing stations 20 defined on the periphery of a continuously rotating hub 22 that is rotated about a fixed vertical axis defined by shaft 24. The containers continue their movement along the path defined by the outer periphery of hub 22 where the actual inspection occurs and, after the inspection is completed, the containers are delivered to an outlet conveyor 26 that defines a continuation of the container path. Container bodies with imperfections are delivered to a reject chute 28, as will be described later.

Figure 3:
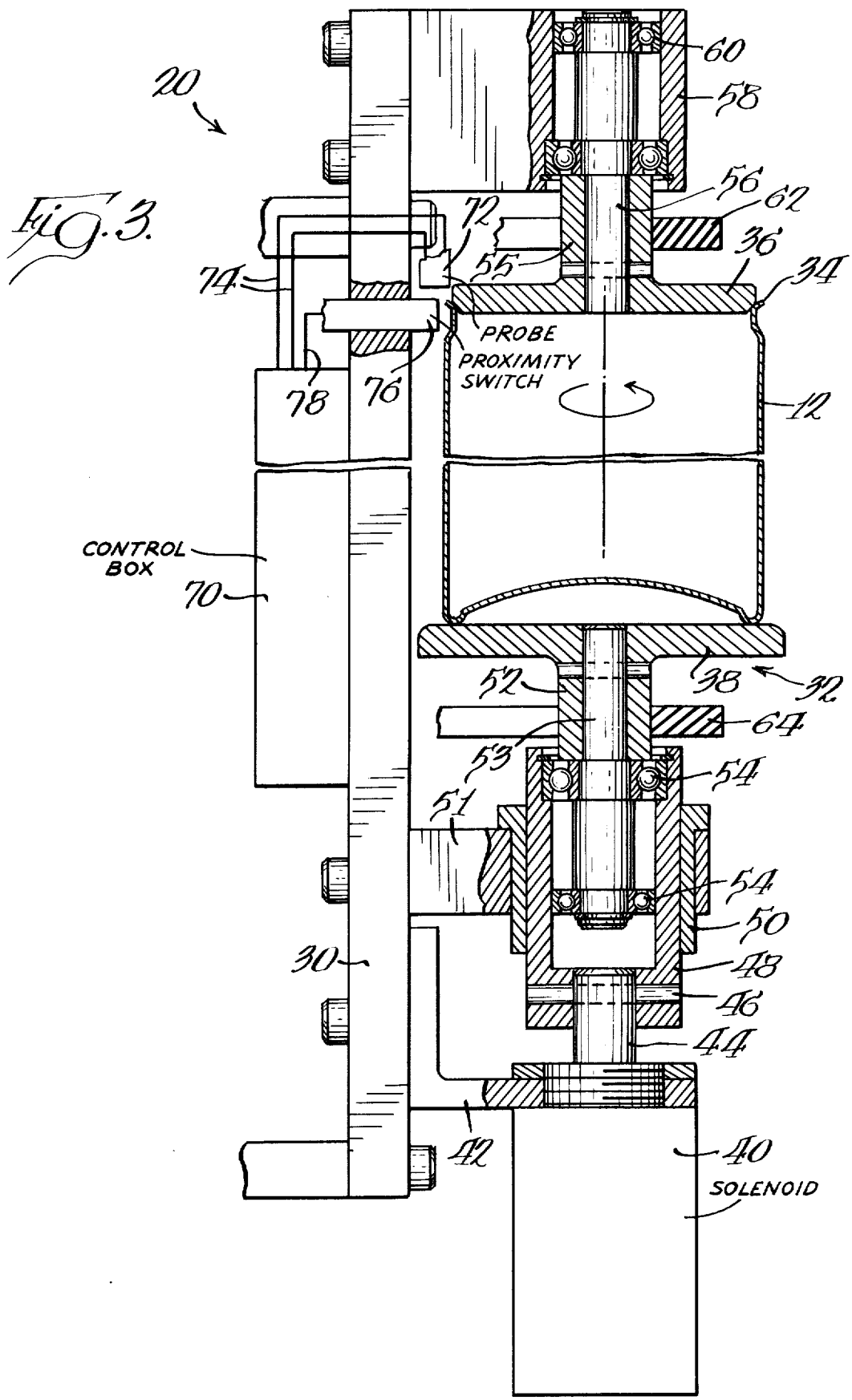
FIG. 3 is an enlarged sectional view of one of the test stations of the apparatus shown in FIG. 1.

Each testing station 20 is preferably a self-contained module that includes all of the electronic circuitry as well as the mechanical holding means so that testing stations can readily be removed and replaced in a short period of time. The details of testing station or self-contained module 20 are illustrated in FIG. 3 and consists of a support 30 that is adapted to be attached directly to the periphery of hub 22 by suitable bolts. Testing station 20 includes holding means 32 for holding a container body 12, such as an open ended drawn and ironed container, having an upper peripheral flange 34 which is the portion of the container body to be tested. Holding means 32 consists of upper and lower discs 36 and 38 which are adapted to engage opposite ends of container body 12. More specifically, lower disc or platform 38 is adpated to be moved towards and away from upper disc 36 which is configured to be received into the open end of container body 12 adjacent flange 34. Discs 36 and 38 are thus capable of holding container body in a fixed position with respect to support 30.

In the illustrated embodiment, the means for raising and lowering platform 38 includes a solenoid 40 secured to support 30 through a fixed bracket 42 with core 44 of solenoid 40 attached to platform 38 through structure that will now be described. Core 44 is connected through a pin 46 to the lower end of a hub 48 that is reciprocated within a sleeve 50 fixed with respect to support 30 by a bracket 51. Platform or disc 38 has a hub 52 which receives shaft 53 and shaft 53 is supported for rotation within hub 48 through suitable bearings 54. Thus, energizing solenoid 40 will raise platform 38 to force container body 12 upward into engagement with upper disc 36, which is also freely rotatable about a fixed axis as will now be described.

Upper disc 36 has an integral hub 55 having a shaft 56 secured thereto and shaft 56 is rotatably supported in a sleeve 58 fixed with respect to support 30 with suitable bearings 60 interposed between sleeve 58 and shaft 56. Shafts 52 and 56 are positioned to be in axial alignment with the center of the circular metal container body 12 so that holding means 32 is freely rotatable about a fixed axis on support 30.

The means for rotating the container body may take various forms but in the illustrated embodiment, this means is again an extremely simple construction requiring no additional power source. In the illustrated embodiment shown in FIGS. 1 and 3, the rotating means consists of a resilient belt 62 that is fixed with respect to the path for the container bodies as they are being moved by testing apparatus 10. As seen in FIGS. 1 and 3, belt 62 extends around the portion of the path for container bodies 12 defined by test apparatus 10 and is positioned to engage hub portion 55 of upper disc 36. Thus, the belt or fixed member 62 will produce rotation of holding means 32 about the center axis of container body 12 as the container body is being moved along the portion of path defined by test apparatus 10. Rotating means may include a second fixed belt 64 engaging lower hub 52.

Each test station 20 also includes a control box 70 that houses the electrical circuitry for the test station. Control box 70 is attached to a probe or fixed inductor means 72 through a pair of wires 74 and probe 72 is fixedly secured to support 30 to be in a predetermined position with respect to upper disc 36 and therefore the peripheral flange 34 to be inspected.

Control box 70 also is attached to switch means in the form of a proximity switch 76 through a further wire 78. Switch means 76 is secured in a fixed position with respect to support 30 and produces a signal when container body 12 is within holding means 32 and in a test position.

Control box or circuit 70 incorporates an eddy current tester that includes an alternating voltage source (not shown) that produces a high-frequency primary alternating current of substantially constant rms value which is supplied to the probe of fixed inductor means 72 through wires 74. This results in a substantially constant magnetic field being developed adjacent the outer end of the probe. The magnetic field developed adjacent the outer end of the probe 72 produces a plurality of flux lines which may be visualized as streaming from the end of the probe, bending around the probe and entering from the opposite end so that the resultant magnetic field is in the form of a doughnut adjacent the end of the probe. Peripheral flange 34 is positioned in a test position by holding means 32 so that flange 34 intersects the magnetic field generated by the inductor means or probe 72.

Probe 72 may be considered the primary winding of a transformer wherein the test piece or flange 34 is the secondary winding for the transformer. Any flux that penetrates flange 34 induces an eddy current, the area of penetration which sets up its own magnetic field. A portion of the magnetic field which is set up by the eddy current intercepts the probe and induces a secondary current in the coil of the probe opposing the primary current.

If flange 34 has any imperfections, such as scratches or dents, the eddy current must follow a path of relatively higher resistance and the rms value of total current flowing in probe 72 will be varied. This rms value is constantly being compared with a reference value within eddy current tester 80 and, when the variations exceed a certain level, eddy current tester 80 produces an output signal that is delivered to gating circuit 82 and, assuming a container body is being detected in a test position by proximity switch 76, produces an output signal indicating an imperfection in the flange. In the illustrated embodiment, the reject circuit 84 may be in the form of a timer which delays the de-energizing solenoid 40 so that container body 12 having an imperfection on flange 34 will be contained in holding means 32 a predetermined additional time period sufficient for the container to be moved out of the path and into the reject chute 28.

Considering now the operation of the testing apparatus 10, container bodies 12 are moved along the path defined by inlet conveyor 14 and are vertically aligned with platform or lower disc 38. At this time a switch (not shown) is actuated to energize solenoid 40 and raise platform 38 with container body supported thereon so that disc 36 is received into the open end of container body 12 and the container body 12 is thus held in a fixed position with respect to support 30. Continued movement of the container body 12 along the path by rotation of hub 22 will produce engagement between hub portion 55 and belt or fixed member 62 so that holding means 32 will be rotated about the axis for container body 12.

Assuming that eddy current tester 80 is energized, resulting in the magnetic field discussed above adjacent the end of probe 72, a voltage will be generated in the metallic can body 12 that will produce an eddy current within the container body which opposes the original current in the probe. The current that is being detected by eddy current tester 80 will be the difference between the normal rms current within probe 72 and the eddy current developed within container body 12. The rms value of the total current is then compared with a reference value within eddy current tester 80 and an output signal is produced when the differences between the two values exceed a certain level. This output signal or reject signal is then fed to solenoid 40 and delays de-energizing the solenoid a sufficient period of time to allow test apparatus 10 to move the defective container body from the path into reject chute 28.

As can be seen from the above description, the present invention provides a unique testing apparatus wherein a selected portion of the container body may be checked for imperfections while the containers are being moved along the path in a production line. By way of example, if there are fifteen test stations located on the periphery of hub 22, and hub 22 is rotated at a speed of 40 revolutions per minute, 600 containers can be tested for each minute of operation. This can be accomplished by limiting the amount of movement for container bodies 12 from the lowered position to the raised position in the test station. For example, it has been found that the container body may be locked between upper and lower discs by only approximately ¼ inch of vertical movement of lower disc or platform 38. Of course, the number of rotations of the container body during the movement along the test apparatus portion of the path may be varied by proper selection of the diameter of hub portions 53 and 55.

A slightly modified form of the invention, particularly the holding means, is shown in FIGS. 4–6. The holding means illustrated in FIGS. 4–6 includes upper and lower pairs of contoured rollers 100 and 102 supported for rotation on fixed brackets 104 that are carried by fixed support 30a. The upper contoured rollers 100 have a radially extending flange 106 that is adapted to engage the upper surface of the container body and a contoured periphery 108 which cooperates with the reduced neck portion 110 adjacent flange 112 of container body 12a. Contoured rollers 102 likewise have a radially extending flange 120 at the lower end which is adapted to engage the bottom edge of container body 12a and the container bodies are held in engagement with the rollers 100 and 102 by fixed guides 122 that extend around a portion of the test apparatus that defines the path for the containers. In this embodiment, the rotation of the containers is again accomplished by a belt 124 which may be fixed as in the previous embodiment of alternatively, may be driven in the direction opposite to the rotation of test apparatus 10 to produce the resultant rotational movement. As in the previous embodiment, the probe 72 and proximity switch 76 would be positioned so that they are in a fixed position with respect to the holding means including rollers 100, 102 and fixed guides 122. The operation of the apparatus shown in FIGS. 4–6 is the same as that described for the previous embodiment.

While the test apparatus has been shown and described in connection with detecting imperfections in container flanges, it also has utility in detecting other imperfections, such as detecting imperfections in internal coatings and bottom wall configurations of the containers.

What is claimed is:

1. Testing apparatus for detecting an imperfection in a peripheral flange of a cylindrical metal container body comprising: a hub supported for rotation about a vertical axis with said hub having a plurality of like testing stations at circumferentially spaced locations, each testing station being a removable unit including a support secured to said hub; fixed inductor means secured to said support and generating a magnetic field in response to a flow of current in said inductor means having a substantially constant rms value, holding means on each support and engaging upper and lower ends of a container body in a testing station for holding said container body in a position where said peripheral flange intersects said magnetic field generated by said inductor means, receiving means operatively connected to said inductor means for detecting variations in said rms value, switch means on each station cooperating with said holding means and connected to said receiving means for energizing said receiving means when a container body is present in said holding means in a test position; and a stationary belt means extending around the periphery of said hub and cooperating with said holding means for simultaneously rotating a plurality container bodies in respective test stations so that all portions of said flanges intersect said magnetic fields.

2. Testing apparatus as defined in claim 1, in which each said switch means is a proximity switch positioned adjacent a portion of the container body to be tested.

3. Testing apparatus as defined in claim 1, in which each holding means includes a disc received into said container body adjacent said flange.

4. Testing apparatus as defined in claim 3, in which each holding means includes a platform supporting said container body and means for moving said platforms and discs towards and away from each other.

5. Testing apparatus as defined in claim 4, in which said discs and platforms are freely rotatable on the associated support about the axis of said container body and are moved along a predetermined path.

6. Testing apparatus as defined in claim 4, in which each means for moving includes a solenoid cooperating with each platform.

7. Testing apparatus as defined in claim 6, in which said disc and platform at each station are supported for rotation about an axis concentric with the axis for said container body.

8. Testing apparatus as defined in claim 1, in which each holding means includes upper and lower pairs of contoured rollers having radially extending flanges adapted to engage opposite ends of said cylindrical container body and said belt means engages the periphery of said container body for maintaining said container body in engagement with said rollers.

9. Testing apparatus for detecting an imperfection on a wall portion of a cylindrical metal container body comprising a hub adapted for rotation about a fixed vertical axis, said hub having a plurality of like testing stations at circumferentially spaced locations on the periphery therof, each testing station including fixed inductor means generating a magnetic field in response to a current having a substantially constant rms value, holding means for holding a container body in a fixed position where said wall portion intersects said magnetic field produced by said inductor means, said holding means including upper and lower disc means adapted to engage opposite ends of said container with means on said support for supporting said disc means for rotation about a vertical axis and means for moving said disc means toward and away from each other, receiving means operatively connected to said inductor means for detecting variations in said rms value, switch means cooperating with said holding means and connected to said receiving means for indicating the presence of a container body in said holding means in a test position and stationary belt means surrounding at least a portion of the periphery of said hub and engaging at least one of said upper and lower disc means for rotating said disc means and container bodies supported between said disc means to move said wall portions relative to said inductor means.

10. Testing apparatus as defined in claim 9, in which each means for moving said disc means toward and away from each other includes solenoid means for moving said lower disc means towards and away from said upper disc means.

11. Testing apparatus as defined in claim 10, in which each receiving means includes means for producing a reject signal when the variation in rms value of the current in the inductor means exceeds a certan level and said solenoid means is energized to move said lower disc means towards and away from said upper disc means, and in which said reject signal delays de-energizing said solenoid means to delay release of said holding means.

* * * * *